United States Patent [19]

Bankert et al.

[11] 4,397,184
[45] Aug. 9, 1983

[54] METHOD AND APPARATUS FOR TESTING XEROGRAPHIC DEVELOPER MIX

[75] Inventors: Neil R. Bankert; Steven R. Heyer; Lawrence Viele, Jr., all of Boulder, Colo.

[73] Assignee: International Business Machines Corporation, Armonk, N.Y.

[21] Appl. No.: 310,579

[22] Filed: Oct. 9, 1981

[51] Int. Cl.³ .................. G01N 27/00; G01N 33/26
[52] U.S. Cl. .................. 73/432 R; 118/689; 324/452
[58] Field of Search .......... 73/432 Z, 150 R; 118/689; 430/107, 120, 122; 324/452, 457

[56] References Cited

U.S. PATENT DOCUMENTS

| 3,960,738 | 6/1975 | O'Brien et al. | 252/62.1 P |
| 3,970,571 | 7/1976 | Olson et al. | 252/62.1 P |
| 4,010,366 | 3/1977 | Neukermans et al. | 250/282 |
| 4,195,260 | 3/1980 | Sakamoto et al. | 324/204 |
| 4,242,434 | 12/1980 | Hirakura et al. | 430/122 |
| 4,254,203 | 3/1981 | Oka et al. | 430/120 |
| 4,331,184 | 5/1982 | Terashima et al. | 73/432 Z X |

OTHER PUBLICATIONS

*IBM Technical Disclosure Bulletin*, vol. 22, No. 1, Jun. 1979, "Toner/Carrier Charge Measuring Apparatus and Method," by R. E. Marrs, pp. 17-20.
*IBM Technical Disclosure Bulletin*, vol. 23, No. 6, Nov. 1980, "Break-In of Toner/Carrier Mix," by S. C. Crossan and J. A. Thompson, pp. 2230-2231.

*Primary Examiner*—James J. Gill
*Attorney, Agent, or Firm*—Francis A. Sirr

[57] ABSTRACT

Xerographic toner and carrier are analyzed by placing a sample thereof in a closed container, the container having upper and lower nonmagnetic and electrically conductive flat plates separated by nonmagnetic and electrically nonconductive walls, and subjecting the container to a vibratory force, while a voltage simulating an electrostatic image is applied to one plate, and while the charge associate with the other plate is monitored.

18 Claims, 6 Drawing Figures

METHOD AND APPARATUS FOR TESTING XEROGRAPHIC DEVELOPER MIX

DESCRIPTION

1. Technical Field

This invention relates to the field of dry xerographic developer mixtures of toner powder and magnetically permeable carrier beads, and to methods and apparatus for testing the properties of such mixtures.

2. Background of the Invention

Dry xerographic reproduction techniques involve the toning of an electrostatic latent image of one polarity with fine toner powder of the opposite polarity, to thereby form a reverse-reading visual image which is subsequently transferred to copy medium such as paper. Thereafter, the paper's toner image is permanently fused to the paper to form a copy or reproduction.

One known toning or developing station is the magnetic brush developer whereat small magnetically permeable carrier beads are mixed with much smaller nonmagnetic toner particles to triboelectrically charge the beads and the toner to opposite polarities. During this mixing and charging, toner costs the carrier beads and is held there by this opposite charge relationship. Later, as the coated carrier bead engages the latent image, a portion of its toner is attracted from the bead to the image.

It is also known that toner and microcarrier particles, of about the same size, can be formed of substantially the same resin material, the carrier particle including magnetizable particles. In some devices of this type, only the toner particle is transferred to the copy substrate, whereas in others both the toner and carrier are transferred to the paper. U.S. Pat. No. 4,254,203 is exemplary of the latter. This patent suggests that the electrical resistance of the mixture can be measured by placing a portion of the mixture between two members which represent the copier's photoconductor and a magnetic brush developer roller, connecting the two members in a voltage/ammeter circuit, applying pressure to the mixture to simulate actual operation in the copier, and calculating resistance.

In an exemplary reproduction device the latent electrostatic image is of a negative polarity. For this device the carrier and toner must triboelectrically charge negative and positive, respectively.

In most copiers using a two-component developer mix of toner and carrier, the toner is a consumable since toner is carried out of the copier on each copy sheet, whereas the carrier stays within the copier. Thus, carrier life must extend to many thousands of copies before replacement of the carrier is necessary.

Those skilled in the art have provided means whereby a two-component developer mix may be tested in order to sense deterioration of the carrier. U.S. Pat. No. 4,195,260 is an example. This patent suggests that deterioration of carrier beads can be determined by first sensing the amount of toner which coats the carrier beads after mixing. The beads are then subjected to the influence of a means which removes some of the toner. An exemplary means is a stream of air. The amount of toner remaining on the beads is again sensed. Deterioration of the carrier beads is sensed as an increase in the amount of toner remaining. Thus, a comparison of these two signals provides an indication of a need to replace the developer mixture.

The ability of toner and carrier to charge each other can also be tested by agitating the two together, and then pouring the mixture over a charged electric-field slide whose polarity attracts the toner. An electronic circuit, including an integrating amplifier, is connected to the slide and provides a measure of toner charge. Subsequent weighing of the slide provides a measure of the weight of toner which carried this charge. Thus, the charge-to-mass ratio of the toner can be calculated. The *IBM Technical Disclosure Bulletin* of June 1979 at pages 17 through 20 describes this procedure.

U.S. Pat. No. 4,010,366 discloses the use of a Faraday cage to measure a toner particle's charge and mass.

Those skilled in the art have also recognized the need to break-in newly manufactured carrier beads prior to use in a reproduction device. If this is not done, copy quality will likely change as the first few hundred or perhaps thousand copies are made using the new mix.

U.S. Pat. Nos. 3,960,738 and 3,970,571 describe arrangements for artificially aging or preconditioning dry electrophotographic developer. In the former of these patents the developer mix is repeatedly passed through an electrostatic field established by a positive or a negative electrode and a grounded electrode. Some of the toner particles are attracted from the carrier beads to an electrode whose polarity is opposite that of the toner. New toner is added, and the process is repeated. After a few hours, the developer mix has been preconditioned for use in a reproduction device.

The latter of these two patents suggests that artificial aging or preconditioning of dry electrophotographic developer operates to pack the pores of the carrier beads with toner, to scum the surface of the carrier beads with a charge control agent, and to abrade the surface of the carrier beads.

Yet another way to break in toner/carrier mix is suggested by the *IBM Technical Disclosure Bulletin* of November 1980 at pages 2230 and 2231. Here a Faraday cage technique is used to monitor the ability of toner and carrier to charge each other as they are agitated together in a container.

The need to test developer mix constituents is further exemplified by U.S. Pat. No. 4,242,434 wherein an insulated test cell is filled with carrier composition. This test cell includes top and bottom disposed electrodes which are connected in a series circuit comprising an ammeter and a battery. The carrier is retained in the cell by the effect of a magnet. The ratio of current to the battery voltage is a measure of the conductivity of the carrier composition.

THE INVENTION

The present invention provides a method and apparatus whereby a known quantity of developer mix is confined to a volume or space from which it cannot escape. The developer mix is then subjected to mechanical agitation similar to that which occurs in the developing station of a reproduction device. The mix within the volume is at the same time subjected to an electrostatic field which facilitates collection of charged toner particles, just as a copier's latent electrostatic image operates to collect charged toner particles on the photoconductor.

More specifically, the volume or space comprises a closed container made up of a pair of parallel, flat, nonmagnetic metal plates separated by nonmagnetic, electrically insulating walls. Preferably this container is supported with its metal plates horizontal. A pair of electromagnets, exterior of the container, and adjacent the two plates, provide an alternating magnetic field which subjects the confined developer mix to mechanical agitation, causing the mix to alternately strike the upper and then the lower plate. In a preferred embodiment, the upper plate is connected to DC voltage of a polarity opposite that of the toner, and preferably of a magnitude which subjects the developer mix to an electrostatic field representative of the reproduction device's latent image. As a result, toner leaves the carrier and deposits on the upper metal plate in a manner analogous to that which would occur had the mix been used in the reproduction device.

The lower plate is connected to a charge measuring circuit in the form of a resettable integrating amplifier. The electrical output signal from this circuit varies as a function of time, and is analogous to the ability of the toner and carrier to interact triboelectrically, and to the ability of the toner and carrier mix to tone a photoconductor's latent image to an acceptable optical density.

Preferably, operation of the measuring circuit is synchronized to alternation of the magnetic field such that the lower plate's charge is sampled once when the developer mix strikes the lower plate, and again when the mix leaves the lower plate on its way to the upper plate. Means are provided at the end of the test to insure that the magnetic field alternation stops at a time when the mix has been attracted to the lower plate.

Preferably, the aforesaid electromagnets are constructed and arranged to concentrate the mixture's vibrating force in a zone which does not include the side walls of the container. In this manner, the mix does not strike the side walls.

A modification of this invention provides for the presentation of a clean upper electrode surface after one or more impacts thereon by the developer mix. In this manner, the toner which has heretofore desposited on the upper electrode can be retained for analysis of the toner's characteristics, for example particle size. In addition, the strength of the electrostatic field can be changed, as a clean electrode is presented, in order to facilitate analysis of the effect of such a change on toner deposition. This function of presenting a clean electrode occurs when the developer mix is not present at the upper electrode, i.e. when it is present at the lower electrode.

Since it is possible for toner to include particles which triboelectrically charge to the wrong polarity, a further feature of the present invention provides for the presentation of a clean bottom electrode. Here again this function is synchronized with mix movement, and occurs when the mixture is not present at the bottom electrode. In this way, the previously used bottom electrode can be analyzed for the extent, size, etc. of this wrong-charging toner.

The foregoing and other features and advantages of the invention will be apparent from the following more particular description of preferred embodiments of the invention, as illustrated in the accompanying drawing.

DESCRIPTION OF THE PREFERRED EMBODIMENTS

Figure 1:
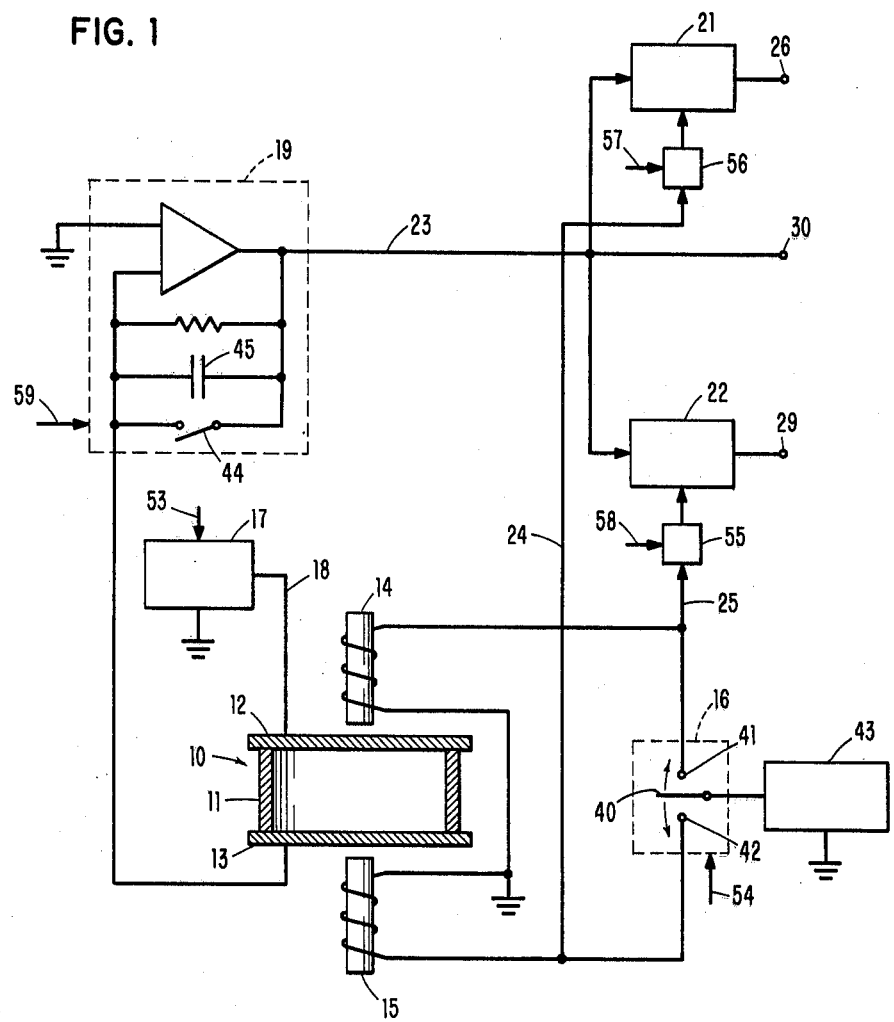
FIG. 1 is a schematic showing of a first embodiment of the present invention.

The FIG. 1 embodiment of the present invention includes a closed sample container 10. This container comprises an annular side wall member 11, preferably formed of the Delrin brand of acetal resin, a nonmagnetic and electrical insulating material. The container is closed by upper and lower flat, circular metal plates or electrodes 12 and 13, preferably formed of brass, a nonmagnetic and electrically conductive material.

The apparatus of FIG. 1 is useful for measuring the operational characteristics of any mixture of xerographic toner and carrier. When used to measure the characteristics of a toner/carrier mixture where the toner-to-carrier size ratio is in the range of 1 to 25, the container is preferably of the dimensions 2.5 cm in diameter and 1 cm in height. When used to measure the characteristics of a microcarrier mixture, wherein the toner/carrier mixture is of a size ratio of about 1 to 1, the container is preferably of the dimensions 2.5 cm in diameter and 0.625 cm in height. In either case, it is preferred that the mixture sample to be analyzed occupy about 1% of the volume of container 10.

Container 10 is completed by a nonmagnetic and electrically insulating clamping means (not shown) which firmly clamps plates 12 and 13 to wall member 11, to form a closed container from which the toner/carrier mixture cannot escape.

Electromagnets 14 and 15 are mounted at fixed positions closely adjacent the container's upper and lower plates, respectively. These electromagnets are electrically connected to be energized by the output of oscillator-type switching circuit 16. Circuit 16 is preferably a solid-state switch, but for simplicity it is shown as a mechanical switch having a movable blade 40 which moves between two fixed-position contacts 41 and 42. Blade 40 is connected to a source of DC voltage 43. Circuit 16 operates to sequentially energize one electromagnet and then the other electromagnet in accordance with a preselected timed sequence of operation. In order to move the toner/carrier mixture from the lower plate to the upper plate, electromagnet 14 is energized and electromagnet 15 is deenergized. This apparatus comprises a vibratory means which is associated with container 10 so as to cause the container's toner/carrier mixture to alternately impact the upper and lower electrodes by virtue of the interaction of the alternating electromagnetic field and the mixture's magnetic carrier constituent. While not critical to the present invention, circuit 16 preferably operates at a frequency of about 7 cycles per second as provided by a 75-millisecond pulse (i.e., 7 impacts at each of the electrodes during one second).

Upper plate 12 is connected to a source of DC voltage 17 whose polarity at conductor 18 is opposite that of the triboelectrically charged toner within container 10.

The portion of the FIG. 1 embodiment thus far described is constructed and arranged to simulate the operational environment of a xerographic copier within which the toner/carrier mixture will be used. Thus, in accordance with the present invention, parameters such as the size of container 10, the toner-to-carrier concentration of the mixture being tested, the magnetic field strength of electromagnetics 14 and 15, the frequency of circuit 16, and the polarity and magnitude of the voltage on upper electrode 12 will be selected in accordance with criteria well known to those of skill in the art. For example, if the copier's electrostatic latent image is negative 800 volts, then power supply 17 is constructed and arranged to provide this polarity and magnitude to upper electrode 12. Also, the electromagnetics cause the toner/carrier mixture to impact upper electrode 12 with a force which is analogous to the force with which the copier's developing station causes the toner/carrier mixture to impact the copier's photoconductor.

The toner/carrier mixture within container 10 is preferably triboelectrically charged prior to use of the apparatus of FIG. 1. This can be accomplished by shaking the mixture prior to loading container 10, or alternatively by a short time period of energization of electromagnets 14 and 15 while power supply 17 is disconnected from electrode 12.

Lower electrode 13 is connected to the input of resettable integrating amplifier 19. Output 23 of this converter is connected to the inputs of two sample-and-hold circuits 21 and 22.

The ability of circuits 21 and 22 to sample the voltage at conductor 23 is synchronized to operation of vibratory means 14, 15, 16 by the signal on conductors 24 and 25, respectively. More specifically, the signal on conductor 24 insures that sample-and-hold circuit 21 is enabled to respond to the voltage on conductor 23 only when the toner/carrier mixture initially strikes lower electrode 13, and the signal on conductor 25 insures that sample-and-hold circuit 22 is enabled to respond to the different voltage on conductor 23 when the toner/carrier mixture thereafter leaves the lower electrode, on its way up to upper electrode 12.

The physical phenomenon associated with vibration of the toner/carrier mixture between plates 12 and 13 is theorized to be as follows. It is believed that the mixture initially comprises, for example, negatively charged carrier particles and positively charged toner particles, with the totality of the mixture being essentially of a neutral polarity. When this mixture first impacts the negative upper plate, a portion of the positive toner electrostatically attaches to the upper plate. Thereafter, the magnetic field reverses, sample-and-hold circuit 21 is enabled, and the mixture, minus the toner left on the upper plate, now impacts the lower plate. The totality of this mixture is now of a negative polarity, since it has lost some positively charged toner. As a result, current flows to the input of amplifier 19, this current pulse is integrated, and its integrated output on conductor 23 provides a voltage pulse to sample-and-hold circuit 21. The magnitude of this pulse is proportional to, and indicative of, the total positive charge left behind on the upper plate by the positive toner attached thereto. This voltage pulse appears between terminals 26 and 30. A recorder or a memory oscilloscope and camera can be used to capture this pulse. In the alternative, the magnitude of this pulse can be stored in computer memory as one point on a time-versus-voltage curve to be later visualized by the use of an output printer.

Resetting of integrating amplifier 19 must now occur before reversal of the magnetic field. This is accomplished by a solid state switch. However, for simplicity, a mechanical switch 44 is shown. This switch now momentarily closes to discharge integrating capacitor 45.

Very shortly thereafter the magnetic field reverses, sample-and-hold circuit 22 is enabled, and the mixture leaves lower plate 13 on its way back to upper plate 12. This departure of the mixture from the lower electrode is accompanied by another lower magnitude current pulse which is applied to the input of amplifier 19. As a result, a second integrated voltage pulse appears between terminals 29 and 30.

It has been found that the difference between the peak magnitudes of these two voltage pulses is a most accurate measure of the charge magnitude of the toner deposited on the upper electrode by the prior impact.

Figure 3:
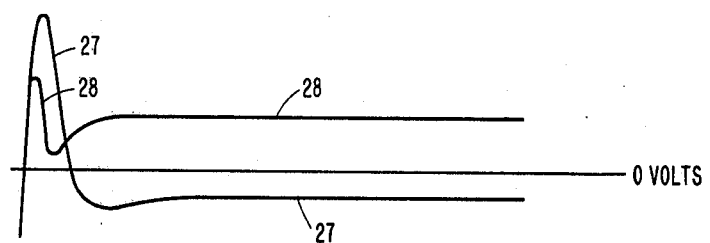
FIG. 3 is an exemplary memory oscilloscope signal trace as provided by the two output signals of FIG. 1.

FIG. 3 shows exemplary memory oscilloscope traces 27 and 28 of the type obtained between terminals 26, 30 and 29, 30, respectively. Those skilled in the art will appreciate that a toner/carrier mixture which is operating to produce copies having good optical density, with good copier performance such as minimum cleaning required of the photoconductor, can be tested to establish a FIG. 3 type reference against which, for example, a newly manufactured mixture may be tested. In addition, reference traces of the FIG. 3 type can be taken of toner/carrier mixtures which exhibit undesirable characteristics, and design modification of the mixture can then be tested in order to determine if the mixture's deficiencies have been corrected. In addition, comparison of the toner quantity collected on upper plate 12 to the carrier quantity resident on lower plate 13, after a period of agitation of the mixture, can be used as a measure of the toner concentration of the original mixture, and more accurately, the toner concentration which is actually available for toning an electrostatic latent image, since any toner which could not be removed from the carrier during such agitation is not actually usable in a xerographic device. These are but three examples of the uses which those skilled in the art will find for the present invention.

FIG. 1 has been intentionally simplified in order to simplify the teaching of the present invention. In practice, those skilled in the art will find it advantageous to provide an electronic sequencer to control the series of events required of the FIG. 1 apparatus. A microcomputer could also be used as a sequencing device.

Figure 2:
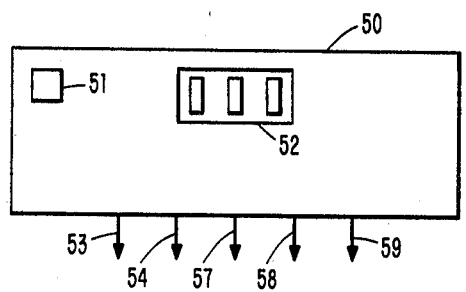
FIG. 2 is an exemplary solid state sequencer which controls the sequence of operation of the FIG. 1 apparatus.

An exemplary sequencer is shown in FIG. 2. Here, sequencer 50 is enabled by start button 51 to begin a test whose duration is determined by the setting of three thumb wheels 52. An exemplary period is 60 seconds.

The initial function to be accomplished by the sequencer is to turn on FIG. 1's power supply 17, as by enabling a signal on conductor 53. A short time delay, such as 20 milliseconds, now occurs in order for the output voltage of this power supply to reach a stable magnitude.

After this delay time has expired, a cyclic, digitized signal on conductor 54, of regular period, operates to first energize FIG. 1's electromagnet 14, and then 15, by controlling solid state switch 16. This signal is unique in two respects. First, electromagnet 14 is the first to be energized, and second, electromagnet 15 is the last to be energized. In this way the end of a 60-second test results in the toner/carrier mix being resident at lower electrode 13. If desired, the test period may terminate by pulse energizing electromagnet 15 once again, i.e. twice in succession, in order to "clean" the container of all carrier beads.

Preferably, sample and hold circuits 21 and 22 are enabled by FIG. 1's conductors 24 and 25, respectively, within a short time delay (represented as 55 and 56 in FIG. 1) after energization of magnets 14 and 15, respectively. This sequencing function is also accomplished by FIG. 2's sequencer 10 and by conductors 57 and 58, respectively. Here the time delay is accomplished by enabling FIG. 1's circuits 55 and 56 a short time period (for example 70 milliseconds) after energization of the related electromagnet. In this manner, the signal on conductor 23, which is sampled at that time, has built up to its maximum integrated value.

The last function to be accomplished by sequencer 10 is to reset the integration function of amplifier 19. This must occur shortly after enablement of a sample and hold circuit, and prior to energization of the next-to-be-energized electromagnet. More specifically, output conductor 59 provides a cyclic, digitized signal, of the same cyclic rate as the signal on conductor 53 but phase displaced therefrom, such that FIG. 1's capacitor 45 is shorted by switch 44, and thus discharged, after the voltage on conductor 23 has been sampled and stored, but before the signal on conductor 54 reverses the magnetic field of electromagnets 14, 15.

As can be readily appreciated, the signals 53, 54, 57, 58 and 59 repeat, in a uniform cyclic manner, until the end of the test period, whereupon signal 54 insures that electromagnet 15 is the last of the two electromagnets to be energized.

Figure 4:
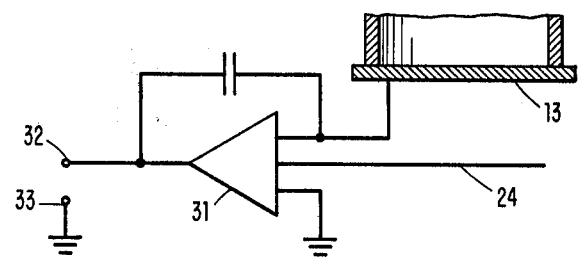
FIG. 4 is a schematic showing of a second embodiment of the present invention.
Figure 5:
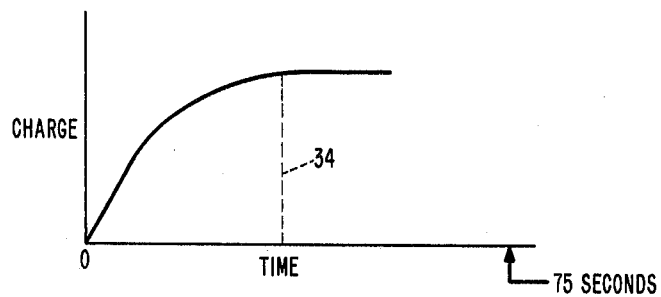
FIG. 5 is an exemplary memory oscilloscope signal trace as provided by the single output signal of FIG. 4.

The FIG. 4 embodiment of the present invention provides an integrating amplifier 31 connected to lower electrode 13, such that output terminals 32 and 33 provide the FIG. 5 plot of the charge left on upper electrode 12 as a function of a time period, for example 75 seconds, during which a number of oscillations of the mixture between plates 12 and 13 has occurred. In this embodiment, a sequencing output conductor 24 operates to enable amplifier 31 only when the mixture strikes lower electrode 13. In the exemplary curve of FIG. 5 it is noted that toner continued to accumulate on the upper electrode from time zero, when the test began, until the time represented by dotted line 34. As an exemplary use of this embodiment of the present invention, the slope of the portion of the curve from time zero to time 34, and the time interval, can be established for a "good" mixture, and thus provide a reference for testing other mixtures.

It is preferred, in accordance with the present invention, that the magnetic field provided by electromagnetics 14 and 15 be confined to a central, vertical zone of container 10 which does not include wall member 11. This can be accomplished, for example, by providing electromagnets which are relatively small, and which are located on the axis of the circular cylinder defined by wall member 11, as shown in FIG. 1. In this way, the mixure does not physically engage wall member 11, such engagement having no analogy to use of the mixture in the xerographic copier for which it is intended.

Figure 6:
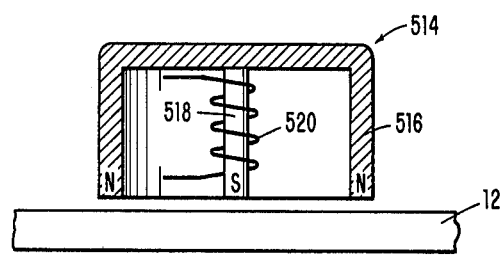
FIG. 6 is a showing of a preferred embodiment of FIG. 1's electromagnet means for mechanically agitating the developer mix within the container of FIGS. 1 and 4.
Figure 6:
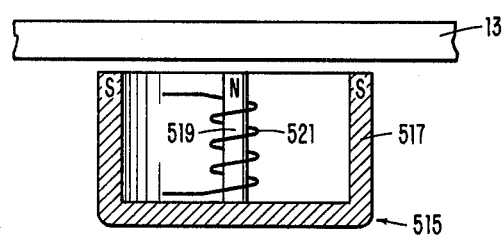

Another form of electromagnet useful in the present invention is shown in FIG. 6, wherein size is not shown proportional to actual practice. In this case, electromagnets 514 and 515 correspond to FIG. 1's electromagnets 14 and 15, respectively. Electromagnets 514 and 515 are cup-shaped, and comprise an annular pole piece 516 or 517, and a central, post-like pole piece 518 or 519. These annular pole pieces, and the central pole pieces, are centered on the relatively much larger electrodes 12 and 13.

The various pole pieces of FIG. 6 bear magnetic polarities showing the instant of magnetic field switching, when, for example, coil 520 is energized as coil 521 is deenergized. With the opposing field polarity, as shown, the carrier beads or particles within container 10 will leave electrode 13 and will move toward electrode 12, as they are confined generally to the cylindrical volume defined by the two annular pole pieces 516 and 517. As a result, the developer mix will not impact the side walls of the container. A moment thereafter, only coil 520 is energized, and only electromagnet 514 retains the indicated magnetic polarity. However, during the time of mix movement, from bottom plate 13 to top plate 12, the magnetic field strength of electromagnet 514 is increasing, as the field strength of electromagnet 515 is decreasing. The interaction of these two fields confines the developer mix to the center non-wall portion of the container.

By way of example, the operational amplifier used in resettable integrating amplifier 19 may be the brand 503 by Analog Devices Company, and sample-and-hold circuits 21 and 22 may be the brand SHM-IC-1 by Datel Company.

While the invention has been particularly shown and described with reference to preferred embodiments thereof, it will be understood by those skilled in the art that various changes in form and details may be made therein without departing from the spirit and scope of the invention.

What is claimed is:

1. Apparatus for measuring the operational characteristics of a mixture of xerographic toner and carrier, comprising:
   a substantially closed container having a first electrically conductive electrode and a second electrically conductive electrode joined by electrically insulating walls, said container being adapted to hold a sample mixture of the toner and carrier;
   vibratory means associated with said container operable to cause the toner and carrier within said container to alternately impact said first and second electrodes;
   a source of direct current voltage connected to one of said electrodes operable to establish an analog of an electrostatic latent image to be developed by the toner; and
   a charge measuring means connected to the other of said electrodes.

2. The apparatus defined in claim 1 including means synchronizing said vibratory means and said measuring means such that said measuring means is operable only when the mixture would be resident at said other electrode.

3. The apparatus defined in claim 1 wherein said vibratory means comprises electromagnetic means, and said electrodes and walls are nonmagnetic.

4. The apparatus defined in claim 3 wherein said electromagnetic means cooperates with said container in a manner to restrict the mixture's vibratory force to a zone which does not appreciably include said walls.

5. The apparatus defined in claim 3 or 4 including means synchronizing energization of said electromagnetic means and said measuring means such that said measuring means is operable only when the mixture is resident at said other electrode.

6. The apparatus of claim 3 or 4 including means synchronizing energization of said electromagnetic means and said measuring means such that said measuring means is operable only when the mixture is resident at said other electrode, and means operable to insure that interruption of energization of said electromagnetic means occurs only when the mixture is resident at said other electrode.

7. Apparatus defined in claim 1 wherein said charge measuring means includes a first and a second signal sampling means, and means synchronizing operation of said vibratory means to operation of said first and second sampling means such that said first sampling means is operative when the mixture arrives at said other electrode, and said second sampling means is operative when the mixture subsequently leaves said other electrode.

8. The apparatus defined in claim 7 wherein said vibratory means comprises electromagnetic means, and said electrodes and walls are nonmagnetic.

9. The apparatus of claim 8 wherein said electromagnetic means cooperates with said container in a manner to restrict the mixture's vibratory force to a volumetric zone which does not appreciably include said walls.

10. The apparatus of claim 1 wherein said charge measuring means includes charge integrating means.

11. The apparatus defined in claim 10 wherein said vibratory means comprises electromagnetic means, and said electrodes and walls are nonmagnetic.

12. The apparatus defined in claim 11 wherein said electromagnetic means cooperates with said container in a manner to restrict the mixtures vibratory force to a zone which does not include said walls.

13. The apparatus of claims 1, 2, 3, 4, 7, 8, 9, 10, 11 and 12 wherein said first and second electrodes are substantially flat and are oriented horizontally when in use, and wherein said first electrode is located above said second electrode.

14. The apparatus of claim 1 wherein said charge measuring means includes a resettable integrating amplifier, and a first and a second signal sampling means to respectively sample and hold the output of said integrating amplifier, and means synchronizing operation of both of said sampling means and resetting of said integrating amplifier to operation of said vibratory means, such that said first sampling means is operative when the mixture arrives at said other electrode, said integrating amplifier is thereafter reset, said second sampling means is thereafter operative when the mixture later leaves said other electrode, and said integrating amplifier is thereafter again reset.

15. The apparatus defined in claim 14 wherein said vibratory means comprises electromagnetic means, and said electrodes and walls are nonmagnetic.

16. A method for analyzing the operational characteristics of a mixture of xerographic nonmagnetic toner and magnetic carrier, comprising the steps of:
placing a sample mixture in a nonmagnetic, substantially closed container having oppositely disposed electrically conductive flat plates;
simulating an electrostatic latent image to be xerographically developed by connecting a DC voltage to one of said plates;
subjecting said container to a vibratory force simulating operation of the developer station of a xerographic device; and
monitoring the resulting charge associated with the other of said plates.

17. The method defined in claim 16 including the step of providing an electromagnetic vibratory force which confines vibration of said sample mixture to a volumetric zone which includes only the conductive plates of said container.

18. The method defined in claim 16 or 17 including the step of maintaining the plates of said container horizontal, with said one plate disposed above said other plate.

* * * * *